United States Patent [19]

Lyddy et al.

[11] Patent Number: 4,690,162
[45] Date of Patent: Sep. 1, 1987

[54] METHOD AND APPARATUS FOR REGULATING FLUID FLOW

[76] Inventors: James E. Lyddy, 122 Claremont Ave., Arlington, Mass. 02174; Randall W. Fincke, 23 Chisholm Rd., Winchester, Mass. 01890

[21] Appl. No.: 782,552

[22] Filed: Sep. 30, 1985

[51] Int. Cl.[4] .................. E03B 1/00; F16K 55/14
[52] U.S. Cl. .......................................... 137/1; 251/4; 251/7
[58] Field of Search .................... 251/4, 6–9, 251/285; 137/1; 604/250

[56] References Cited

U.S. PATENT DOCUMENTS

| Re. 31,584 | 5/1984 | Adelberg . | |
|---|---|---|---|
| 1,865,012 | 6/1932 | Jackson | 251/8 |
| 2,167,952 | 8/1939 | Jordan | 251/7 |
| 2,889,848 | 6/1959 | Redmer | 251/7 |
| 2,987,292 | 6/1961 | Teson et al. | 251/6 |
| 3,512,748 | 5/1970 | Wilson | 251/8 |
| 3,685,787 | 8/1972 | Adelberg . | |
| 3,802,463 | 4/1974 | Dabney | 251/6 |
| 3,893,468 | 7/1975 | McPhee . | |
| 4,013,263 | 3/1977 | Adelberg . | |
| 4,047,694 | 9/1977 | Adelberg | 251/7 |
| 4,272,051 | 6/1981 | Huggins | 251/6 |
| 4,307,869 | 12/1981 | Mittleman | 251/7 |
| 4,434,963 | 1/1985 | Russell et al. . | |
| 4,492,360 | 1/1985 | Lee, II et al. | 251/285 |

Primary Examiner—Martin P. Schwadron
Assistant Examiner—Sheri M. Novack
Attorney, Agent, or Firm—Kenway & Jenney

[57] ABSTRACT

A low cost, mechanical method and apparatus for controlling the size of an internal orifice in a deformable tubing, particularly tubing of a viscoelastic material such as PVC used to administer intravenous fluids. A portion of the tubing is clamped to place a portion of the internal walls of the tubing into contact with one another at a plane of contact. The non-contacting portions of the tubing define at least one flow orifice. The contacting portions are then further compressed so that the wall thickness of the contacting tubes is reduced from its initial, unclamped thickness. The degree of this compression is such as to cause the adjacent tubing wall portions to curve away from the plane of contact, preferably with four point symmetry. This condition is also characterized by the stresses within the tube wall tending to expand or contract the orifice being generally in equilibrium within a brief period of time, typically less than five minutes, during which period the orifice usually expands slightly. In a preferred form, two side clamps face one another and are spaced along the tube to produce an orifice that defines a flow path transverse to the tubing. The clamping surfaces adjacent the orifice are preferably rounded or angled, opposed clamp members have abutting surfaces that limit the maximum displacement of the clamp, and an adjustment member is positioned to act on the outer surface of the opened orifice.

31 Claims, 32 Drawing Figures

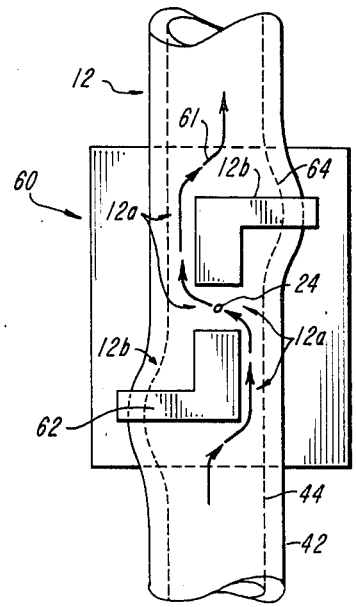
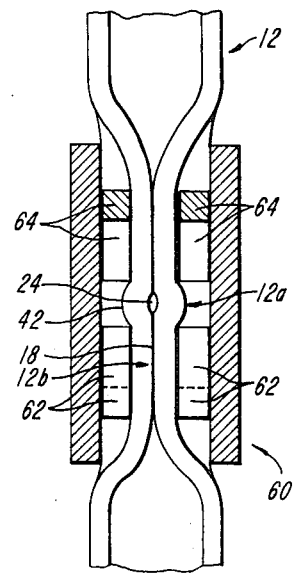
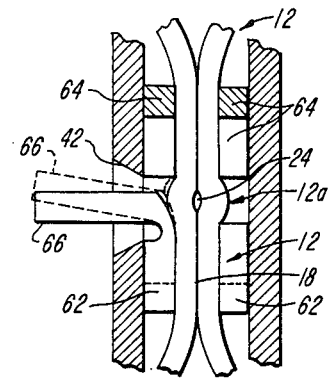
*FIG. 6A*  *FIG. 6B*  *FIG. 7A*
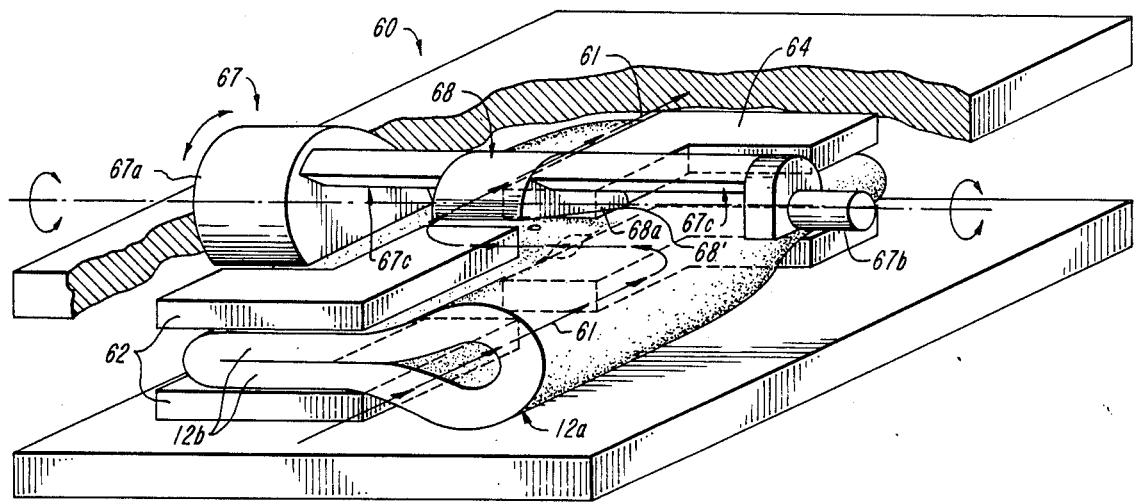
*FIG. 7B*

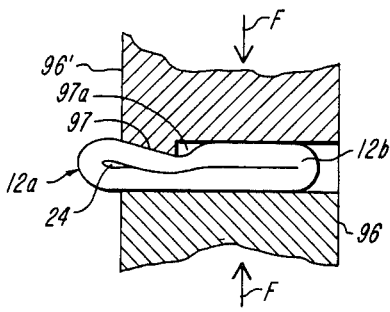
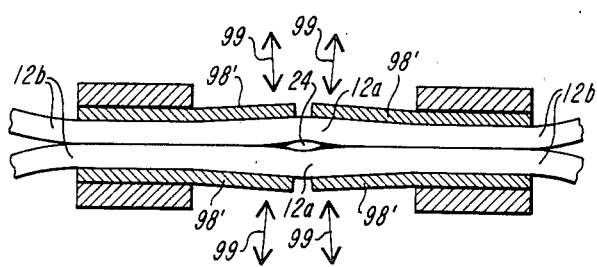
*FIG. 11C*   *FIG. 11D*
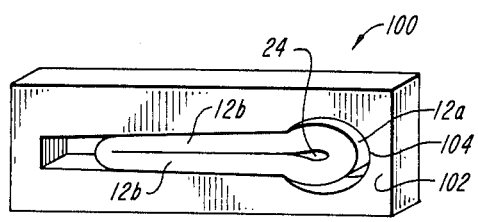
*FIG. 12A*
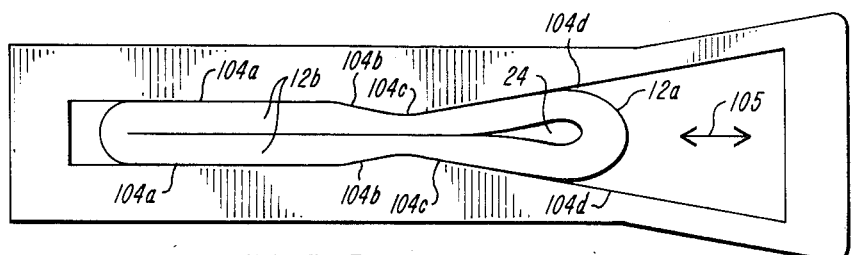
*FIG. 12B*
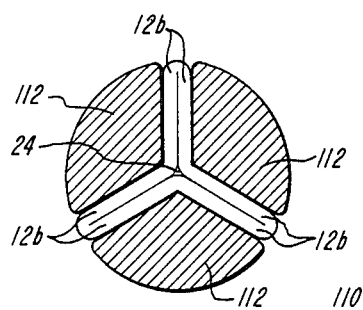
*FIG. 13*

METHOD AND APPARATUS FOR REGULATING FLUID FLOW

BACKGROUND OF THE INVENTION

This invention relates in general to flow control, and more specifically to a novel method and apparatus for regulating the flow of an intravenous fluid to a patient through a deformable tube.

Intravenous (IV) therapy is widely used in hospital care. Approximately 40% of all hospitalized patients receive a solution by IV administration. Intravenous administration has several important medical advantages: providing access to the patient's blood stream for the direct injection of medications; facilitating maintenance of a balanced electrolyte and fluid level; providing a means for controlled delivery of drugs with respect to both dose and timing; and delivering nutritional supplements.

Traditionally, an IV set up consists of a supply bottle or bag, a disposable administration set consisting of polyvinylchloride (PVC) plastic tubing, a drop chamber to allow fluid rate to be set by counting drops and converting to volume rate of flow, a roller or screw clamp that squeezes the tubing to control the size of the internal flow path and thereby controls the flow rate, a Y-site for injection of medications, and a filter for the fluid to be administered. In this set up, fluid flow is driven by gravity, and is a function of hydrostatic pressure head and the pressure drop across the clamp. The hydrostatic pressure is determined by the height of the fluid level above the heart of the patient minus venous pressure. Pressure drop is controlled largely by the cross-sectional area of the flow path restricted by the clamp. Flow rate is set by adjusting the clamp (e.g. by rotating the roller) while counting drops and converting to flow rate using the conversion formula provided by the manufacturer of the intravenous administration set. In the conventional prior art system the flow regulator reduces the flow area at a control site. The clamp can reduce the flow area sufficiently to stop the flow completely, but in all prior art clamps to reopen the flow path the direction of clamping is reversed which ordinarily reduces the clamping force.

A well recognized problem of gravity driven administration sets is inconsistency of the flow rate over time. Numerous clinical studies have been conducted to determine the source of this problem. For example, E. W. Clarke et al. reported such a study in "Impairment of Flow in Routine Gravity-Fed Intravenous Infusions to Surgical Patients" in *Clinical Science,* 57, 515–520 (1979), in which they concluded that the decrease in flow rate was due to the gradual deformation of the plastic tubing under the regulator clamp. Other studies include "Behavior of Standard, Gravity-fed Administration Sets Used for Intravenous Infusion" by F. C. Flash and T. D. White in *British Medical Journal,* 3:439–443 (1974) and "Electronic Flow Control and Roller Clamp Control in Intravenous Therapy" by B. A. Bivens et al in *Arch. Surg.* 70–72 (1980).

This problem is particularly complex and troublesome for viscoelastic plastic materials such as PVC. When the tube is clamped from its initial cylindrical shape, stresses induced by the clamping cause a gradual deformation of the tubing over time known as "cold flow" or "creep". These changes in the tubing result in corresponding changes in the tube flow path dimensions and therefore the fluid flow rate through the flow path. Flow rate is very sensitive to the size of the orifice, varying with the fourth power of the radius and the second power of the cross-sectional area. (Also, the clamp itself can deform over time.) However, since PVC has a significant cost advantage over alternative materials, it continues to be the preferred material for IV administration tubing. The usual solution is to monitor the flow rate and make periodic manual adjustments in the clamp to compensate for the creep and thereby to stabilize the flow rate. This solution, however, is subject to human error, risks substantial variations in flow rates between adjustments, and requires the time and regular attention of a nurse or other health care person.

Examples of prior art clamps are disclosed by U.S. Pat. No. 3,685,787 (now Re 31,584); U.S. Pat. No. 4,013,263; and U.S. Pat. No. 4,047,694 to Adelberg, U.S. Pat. No. 3,802,463 to Dabney, and U.S. Pat. No. 4,434,963 to Russell et al. The '787 patent to Adelberg discloses a roller clamp where a roller is mounted on a shaft that is journaled for movement within two parallel, longitudinally extending grooves. Opposite the roller is a groove, typically V-shaped, with longitudinally varying dimensions that in combination with the position of the roller controls the minimum dimensions of the flow lumen. There is no arrangement for securing the roller reliably in one position along the tubing. The walls of the tube alongside the V-shaped groove are in contact, but only slightly compressed; the purpose is simply to confine flow to the orifice defined by the groove and location of the roller. While this patent attempts to resolve the problem of cold flow of the plastic material at the clamped section, in practice it has not done so reliably.

The '263 and '694 patents teach modified embodiments of the roller clamp of the '787 patent which address the same problems. In the '263 patent, a plurality of ridged elements are formed on the surface of the roller clamp which act locally to pinch or grip the tubing at discrete intervals. In the '694 patent, the tubing is clamped over a variable cross-section longitudinal channel and the edges of the roller wheel are undercut to form stepped shoulders or recesses between the wheel and the side walls of the clamp body so that the tubing can migrate into these areas when there are longitudinal forces acting on the tubing. (It is significant to note that this clamp is designed to push tubing material away from the flow path.) Due to this design which compresses a relatively broad section across the entire width of the tubing, a larger force is required to achieve the same degree of compression than with a narrow or pointed means of compression. This increased force causes creep not only in the tubing, but in the plastic clamp itself, leading to changes in the position of the roller relative to the tubing over time. More generally, this problem is characteristic of all conventional roller clamps now on the market since the roller presents a large surface area in contact with the tubing along a portion of its circumference; thus a relatively large force is required to produce a desired stress in the tubing.

Another problem with this type of clamp is that after cold flow away from the clamped region, the tubing has thinned and the clamping roller is free to "fall" onto the reduced thickness rubbing. This changes the applied force, and the flow rate. Still another problem with conventional roller clamps of the Adelberg type is that if large comressive forces are applied to the tubing, the stress in the tubing walls is substantial and causes creep. In particular, when a round tubing is compressed under a roller against a hollow channel with large compressive forces, the upper tubing wall is under sufficient stress to bow away from the roller toward the flow path, as shown in FIGS. 3b, 7 and 8 of Adelberg Re 31,584. In this situation, the geometry of the flow path is not time stable and the stresses acting within the tubing walls, whether compressive, tensile or shear, are not in equilibrium until the material cold flows to relieve the stresses.

The '463 patent discloses a roller clamp that compresses a longitudinal section of the plastic tubing, leaving the sides uncompressed, thereby forming a pair of side orifices through which the fluid flows. While Dabney attempts to deal with the same general problem as the present invention, in the central compressed section of the tubing, Dabney, like Adelberg, brings the inner walls into contact only to stop the flow (which Dabney terms a "slight compression") and to define a flow lumen where the inner walls are not in contact. Compressing a tubing from an initially circular configuration to the double lumen configuration of Dabney introduces significant internal stresses that over time cause creep and variations in the fluid flow rate through the two side lumens.

The '963 Russell et al. patent discloses a simple slide clamp where the tubing is received in an internal slot with a longitudinally varying gap. Sliding the tubing toward the narrower end of the gap restricts and then closes off a flow through the tubing. Such devices are used as "on-off" clamps, not to produce a variable flow rate and certainly not to produce a flow at a time-stable rate.

In practice none of the prior art devices has provided a reliably consistent, well-controlled, time-stable administration of fluids to a patient using a standard IV administration tubing set without repeated manual readjustment. To date the standard industry solution to the accuracy problem has been in-line flow valves and electronic flow control devices. These devices provide the desired control but they are much more expensive than external clamps of the type shown in the Adelerg or Dabney patents. Thus their use is generally limited to critical care and specialty applications for medical or surgical patients. Heretofore there has been no low-cost IV administration set suitable for routine patient care that also delivers a fluid at a well-controlled rate over an extended period of time.

It is therefore an object of the present invention to provide a method and apparatus that produce a fluid flow rate that is exceptionally stable over an extended period of time and therefore does not require frequent manual readjustment.

It is further object of the present invention to provide a method for controlling fluid flow and a flow control device wherein a stable flow rate is achieved within minutes after initial adjustment and remains generally stable, with less than a 10% change from the initial flow rate.

It is another object of the present invention to provide an inexpensive, disposable, and easily manfactured flow control device and method for using the same.

It is yet another object of the present invention to provide a method for regulating intravenous fluid flow which does not require electronic controllers or in-line devices that come in contact with the fluid.

A further object of this invention is to provide a flow control method and apparatus that provides the foregoing advantages even when the tubing is PVC.

Still another object is to provide a flow control device with the foregoing advantages that requires relatively low force levels to achieve the desired flow control.

SUMMARY OF THE INVENTION

The geometry of tubing formed of a viscoelastic material such as PVC commonly used in IV administration sets is maintained in a well-controlled dimensional state over an extended period of time, despite a strong propensity for viscoelastic material to creep, through a method utilizing only the application of compressive forces external to the tubing. The tubing is compressed in part at a flow control site until at least a portion of the inner surfaces of the walls contact one another in a plane of contact. The walls are then further compressed until the adjacent unclamped wall portions, which define at least one internal orifice within the tubing, curve away from the plane of contact. In the preferred form, this curvature is characterized by a four-point symmetry in that the two unclamped walls curve away from the plane a generally equal amount when examined in planes either perpendicular or parallel to the longitudinal axis of the tubing. This additional compression following wall contact reduces the thickness of both tube walls, a typical value for the reduction being in the range of 15 to 40%. Another characteristic of this invention is that the net stresses, compressive, tensile and shear, within the tube walls following this extra compression are generally in equilibrium after an initial transient state where the orifice cross-sectional area usually increases slightly. This initial orifice growth, measured in cross-sectional area, is typically less than 5%. This corresponds to a flow rate increase of less than 10% and an orifice radius growth of less than 3%.

Various apparatus can implement this method for flow control. In a preferred embodiment, two side clamps are longitudinally spaced along tubing and face one another to apply the aforementioned clamping and compression from opposite sides of the tubing. The clamps extend transversely a suficient distance that they cooperate to define an orifice between two larger diameter lumens located at opposite sides of the tubing where the flow path through the orifice is not parallel to the longitudinal axis of the tubing. Good flow control derives in part from the utilization of longitudinal or "axial" stresses to open the tubing to form the orifice.

In other embodiments, the tubing is positioned between two or more opposing compressive means located at the same point along the length of the tubing. For example, in a simple side clamp two parallel or angled flat plates close and compress a portion of the tubing sufficiently to produce the operational results discussed above. In another form, two opposed clamp members extend transversely across the tubing with opposed recesses in each member defining a central cavity that contains and, in cooperation with the compression of the tubing walls produced by the plates adjacent the cavity, defines a well-regulated, dimensionally time-stable orifice according to this invention. In all of the embodiments, the clamping surfaces adjacent the walls defining the orifice are preferably angled or rounded away from the orifice to reduce the area of engagement with the tubing of the member applying the clamping force to the tubing. Also, the clamping members themselves or auxiliary stop members can limit the maximum compression exerted by the clamp.

An extremely economical embodiment of the invention utilizes a slotted plate with the tubing held in the slot. The side walls of the slot are angled, at least in part, and spaced from one another so that one side of the tubing is closed and compressed, causing the orifice to open as in the other embodiments.

Also in the preferred form there is a mechanical arrangement that acts on the outer surface of the tubing wall surrounding the orifice after the orifice has been formed according to the present invention. In one form, this arrangement is simply a fixed enclosure that limits the maximum size of the opened, orifice-containing portion of the tubing. In another form it is an adjustment mechanism such as a rigid member that contacts the tubing and is movable along its axis, whether in a sliding movement, a lever action, a screw advance, or otherwise. If the member is slidable, there is preferably a set screw or other means to secure a setting. In another form, a rotatable member with a cam control surface is mounted so that the control surface engages the tubing to change the cross-sectional area of the orifice as a function of the angular position of the rotatable member and the associated cam surface.

These and other features and objects of the present invention will be more fully understood from the following detailed description which should be read in light of the accompanying drawings.

BRIEF DESCRIPTION OF THE DRAWINGS

FIG. 6a is a simplified top plan view of the clamp of FIG. 5 indicating the flow path through the tubing;

FIG. 6b is a side view in vertical cross section of the device of FIG. 5 taken along line B—B;

FIG. 7a is a detailed view in longitudinal cross section of the clamp and cam device shown in FIG. 7b at the orifice;

FIG. 11c is a cross-sectional view of a clamp similar to the clamp shown in FIG. 9a but where one plate adjacent the tubing has a portion that is angled inwardly away from the orifice;

FIG. 11d is a cross-sectional view of a clamp similar to the clamp shown in FIG. 11b where the angled barrier plates are adjustable;

FIG. 12a is a view in perspective of a low cost clamp according to the invention;

FIG. 12b is a top plan view of a preferred form of the clamp shown in FIG. 12a;

FIG. 13 is a cross-sectional view of a flow control device for applying compression to the tubing from multiple directions which produces an expanded orifice in the center of the tubing;

DETAILED DESCRIPTION OF THE INVENTION

Figure 1:
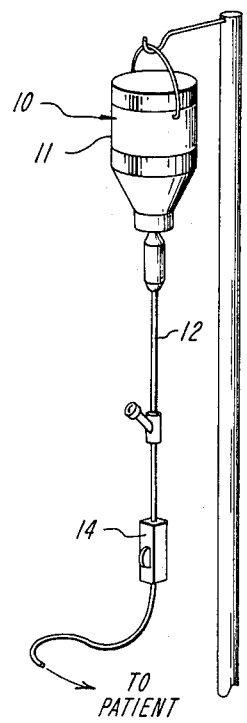
FIG. 1A is a view in perspective of a conventional IV administration set utilizing a flow regulating apparatus according to the invention.

FIG. 1 shows a typical setup for the intravenous (IV) administration of a fluid 10 from a supply bottle 11 through a deformable tubing 12. The tubing is formed of a viscoelastic material such as polyvinylchloride (PVC) which exhibits deformation and hysteresis over time in response to applied stresses on the tubing walls.

The tubing 12 in its normal state is in the form of a hollow tube with generally cylindrical inner and outer surfaces and negligible internal stresses within the walls of the tube.

A principal feature of the apparatus of the present invention is a clamp 14 secured at the exterior of the tubing 12 which creates and controls an internal flow orifice 24 within the tube 12 that regulates a flow of the fluid 10 to a patient. The orifice dimensions are well-regulated and highly stable over time despite the tendency of the PVC material to creep. The clamp 14 can be constructed in a variety of forms, as will be described in detail below. Each embodiment, however, utilizes the method of the present invention which involves (i) clamping a portion or portions of the tubing until the inner walls of that portion or portions meet in an associated plane of contact that blocks a flow of the fluid 10 and creates at least one adjacent flow orifice, and (ii) compressing the walls to cause the adjacent walls of the tube around the orifice to deflect away from the plane of contact, thereby opening the orifice and producing a net stress within the tube walls defining the orifice that is in equilibrium so that the tube walls will not tend to expand or contract over time to any substantial degree.

Figure 2A:
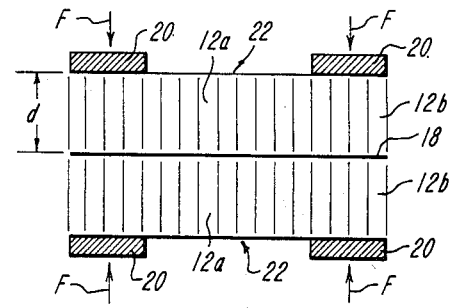
FIG. 2a is a cross-sectional view of two flat sheets of viscoelastic material to which two pairs of opposing compressive plates are applied.
Figure 2B:
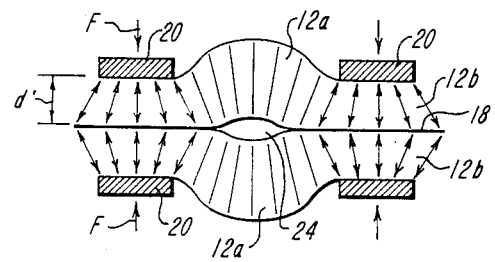
FIG. 2b is a cross-sectional view of the material of FIG. 2a when additional compressive forces are applied according to the present invention.

FIGS. 2a and 2b illustrate this method in a generalized form. Two layers of deformable, viscoelastic tubing material 12 are driven into contact with one another at their opposed inner wall surfaces. A plane of contact 18 is defined by the surface where these inner walls meet. (Note that while the plane 18 is shown as flat, it can also be curved if the closing and compressing forces are applied in a sufficiently non-planar manner.) Opposed pairs of clamping plates 20,20 drive the tubing wall portions 12b,12b into the position shown in FIG. 2a which blocks a fluid flow within the tubing. The left-hand pair of clamping plates 20,20 is spaced laterally from the right-hand pair, as shown, to provide central openings indicated generally at 22,22 located symmetrically at a central section 12a of the tubing walls.

Figure 2C:
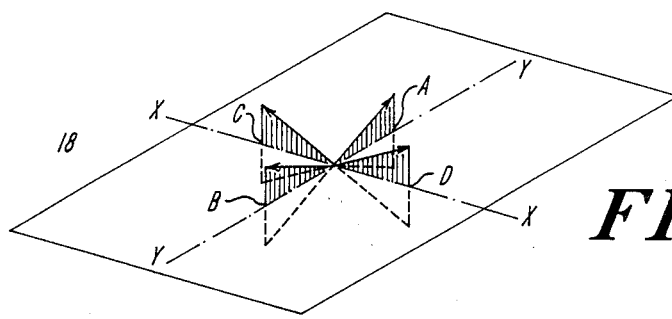
FIG. 2c is a stress vector diagram in perspective illustrating the four point symmetrical opening, both longitudinally and transversely, of the tubing walls in the preferred form of this invention.

In accordance with the present invention, after closing at least a portion of the tubing walls (12b,12b in FIG. 2a), further compressive stress is applied to the wall portions 12b,12b which reduces the wall thickness from an initial value d to a reduced value d' shown in FIG. 2b. As shown, this compressive stress is produced by driving the opposed clamping plates 20,20 toward one another. It has been found that this additional compression causes the unclamped walls 12a,12a adjacent the clamped portions 12b,12b to curve away from the plane of contact 18 as shown in FIG. 2b. It should be noted that the curvature is generally symmetrical with respect to the plane. (While mirror image symmetry is preferable, it is not required.) This is because the stress vectors within the tubing walls 12a, 12a, as shown in FIG. 2c, are generally equal in magnitude and oppositely directed, with respect to a transverse axis x and a longitudinal tubing axis y lying in the plane of contact 18. Looking at the ends of these vectors as points in a three-dimensional plot of the stresses in the tubing during the opening of the orifice 24, this arrangement can be characterized as having a four-point (points A, B, C and D in FIG. 2c ) symmetry with respect to the plane of contact.

Another important characteristic of the present invention is that this additional compression is at a level which causes (i) a central flow orifice 24 to open between the portions 12a,12a and (ii) after a brief initial period of expansion, offsets existing stresses due to the deformation of the tubing from its initial round condition so that the net internal stresses within the wall portions are generally in equilibrium. Because, surprisingly, one can attain this equilibrium state, subsequently only small stresses arise which, over time, can cause the walls 12a,12a to move in a manner that will either expand or contract the cross-sectional area of the orifice 24 slightly. The orifice, and any fluid flow through the orifice, is therefore well-regulated and time-stable.

Figure 14:
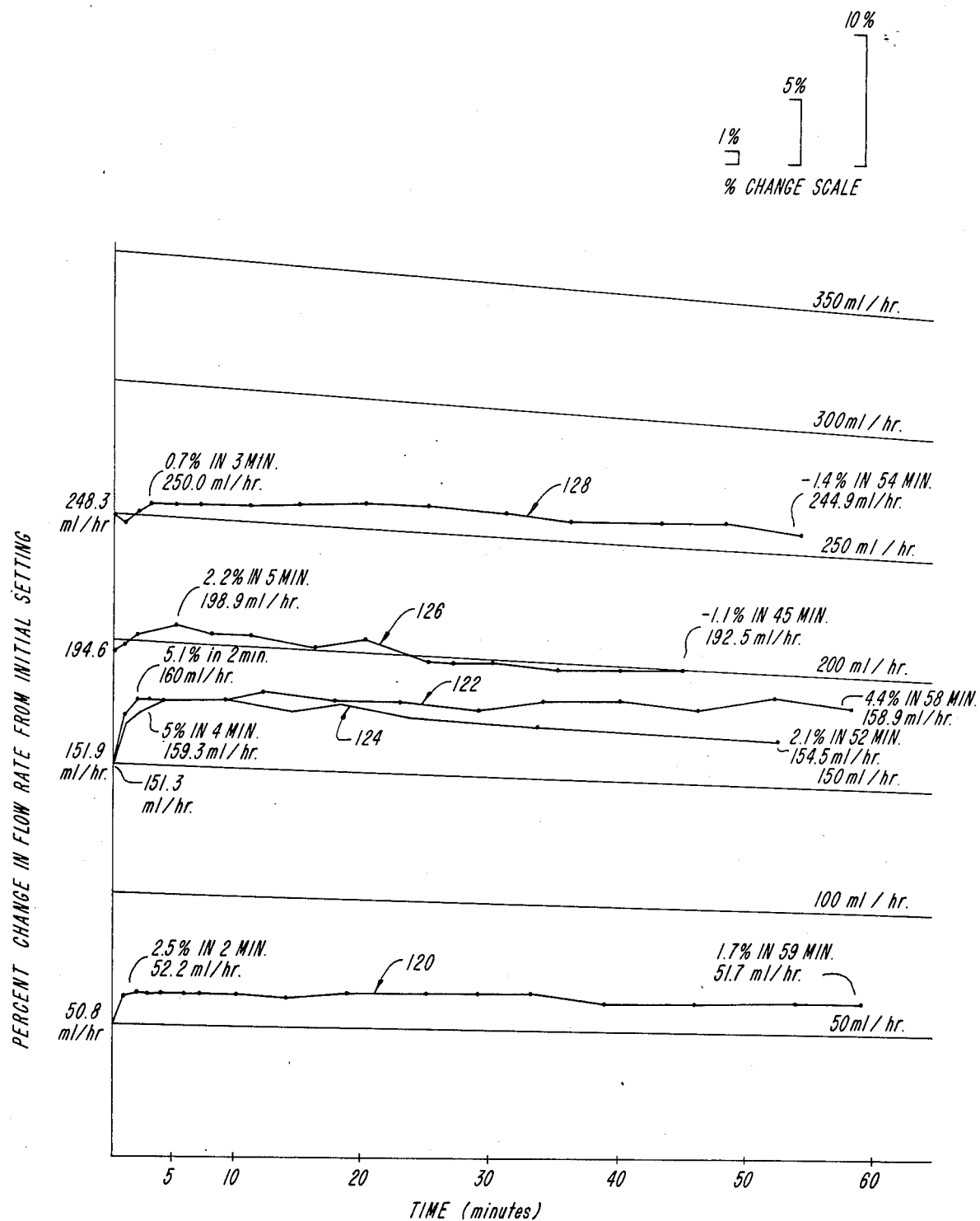
FIG. 14 is a graph of the percent change in flow rate versus time in minutes for clamps according to the present invention.

For typical 0.170 inch PVC tubing used in IV administration, where the closed but uncompressed walls have a thickness $2d$ of about 0.048 inch, the beneficial effects of the present invention have been demonstrated with a compression of the tubing to a value for $2d'$ of about 0.030 to about 0.037 inch depending upon the embodiment of this invention used to achieve this compression. Once the additional compressive stress is applied, the orifice 24 forms. It usually increases slightly in cross-sectional area for up to 15 minutes, with 5 to 10 minutes being typical values. The area increase is typically less than 5%. Thereafter the flow area of the orifice is generally stable, with variations over the normal use of the clamp, at least several hours, typically being within ±10%. The performance characteristics are illustrated in FIG. 14 which is discussed in more detail below.

Figure 3B:
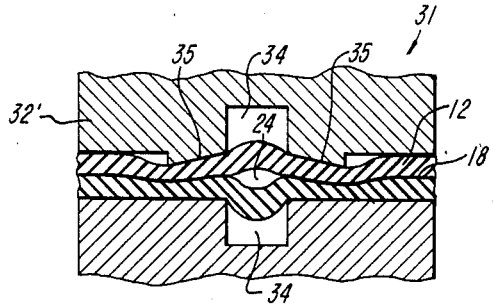
FIG. 3b is a cross-sectional view of the clamp of FIG. 3a wherein the upper compressive plate is angled inwardly away from the cut out section.
Figure 3A:
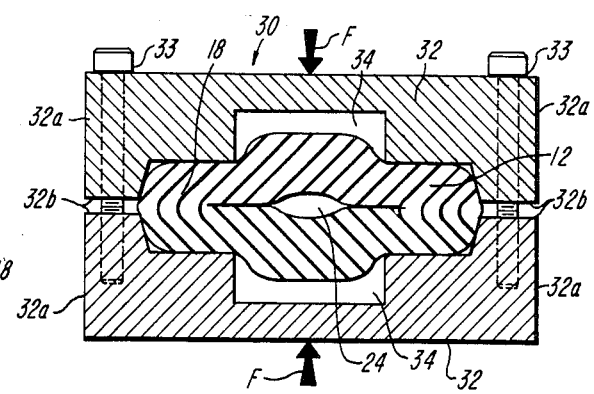
FIG. 3a is a cross-sectional view of a clamp constructed from two parallel opposing plates with opposing central recesses that receive an opened tube with a central flow orifice.

FIG. 3a illustrates a clamp 30 according to the present invention which utilizes the features described with respect to FIGS. 2a and 2b. The clamp 30 has two parallel plates 32, 32 each with an open ended recess 34 that face one another to define a central cavity. Adjusting screws 33, 33 (or any of a wide variety of common expedients) can be used to drive the clamp plates 32, 32 toward one another to produce a force F which closes the tubing 12 and then opens a stable flow orifice 24. For example, the plates 32, 32 can be mounted in a separate frame and the compressive force developed again by set screws acting against springs bending to urge the clamp members to an open position. The plates have end portions 32a that lie outside of the tubing 12. The end portions, in turn, have opposed end faces 32b that meet to limit the maximum compression that can be applied by the screws 33, 33. As will be readily understood, a wide variety of other mechanical arrangements can also produce this limitation on the minimum clamping gap and therefore the maximum compressive stress.

As a specific example of the present invention, the clamp 30 has been constructed using compressive plates with the following dimensions: the length of the recess 34 across the tubing is 0.050 inch, the length of the compression plates across the tubing, including the cut out sections, is 0.170 inch, and the width of the compression plates along the longitudinal axis of the tubing is 0.065 inch. With this clamp, the flow rates through tubing with an outside diameter of 0.170 inch and a wall thickness of 0.024 inch were determined for various degrees of compression. When the gap between the two plates was set at $2d$ or 0.048 inch, there was no flow. At this point the two opposing walls are just touching each other at the plane of contact 18. When the plates were compressed to a resultant tubing wall thickness of 0.037 inch, the flow rate, set initially at 150 mls/hr, stabilized at about 160 mls/hr in less than 3 minutes. A gap of 0.040 inch was found not to generate enough compressive force to stabilize the flow rate. When the plates were further compressed to a thickness of 0.034 inch, the flow rate, initially measured at 240 mls/hr, rose to about 290 mls and then fluctuated for the next hour, but the flow rate was considerably more stable than when the prior art roller devices were used under comparable conditions.

FIG. 3b shows a variation 31 of the clamp 30 wherein the upper compressive plate 32' is angled inwardly away from the cut out section 34 at 35, 35 in order to decrease the total force required to compress the material 12 and thereby decrease the time in which a stable orifice 24 is formed. An inclination of 5 degrees has been found to be effective, but any degree of inclination away from the recsses 34, 34 whether a flat surface or rounded, has the same advantages.

Figures 3C, 4A, 4B, 4C:
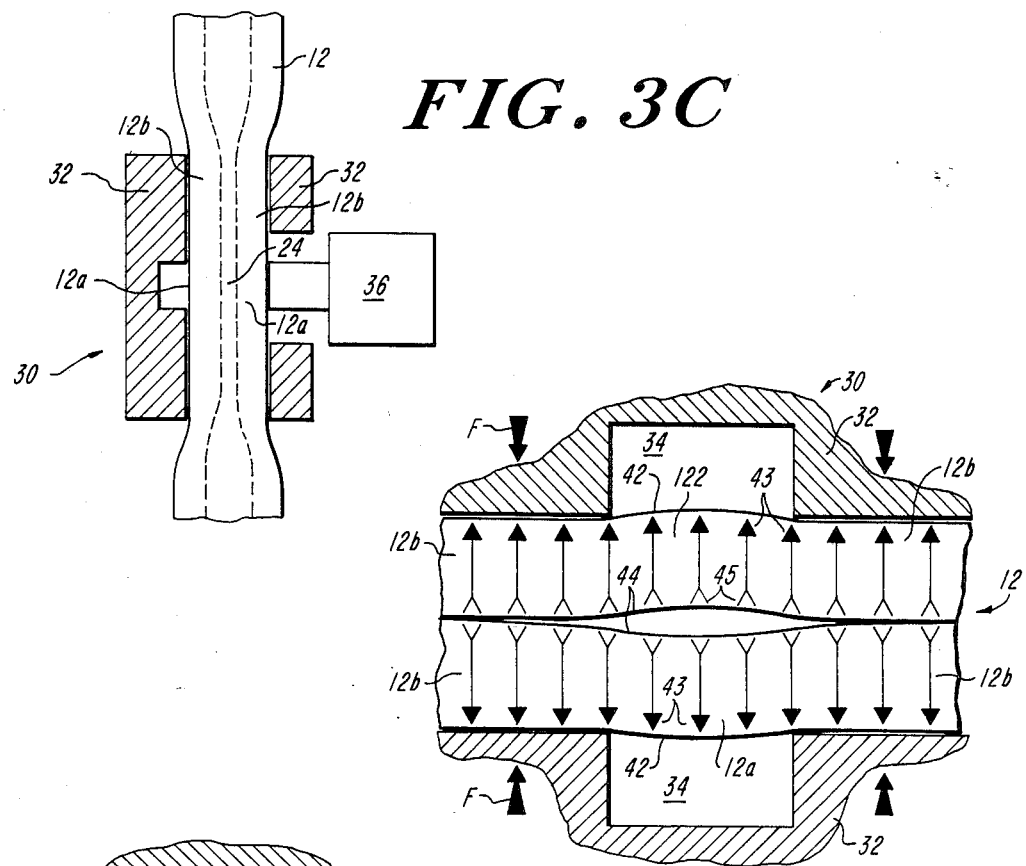
FIG. 3c shows a clamp according to this invention used in conjunction with a transducer to measure fluid pressure within the tubing.
FIGS. 4a-e are cross-sectional views of the clamp of FIG. 3a applied to a section of viscoelastic tubing as the compressive force is increased.

FIG. 3c shows a clamp similar to the one shown in FIG. 3a which is used to create a dimensionally stable section of tubing within the clamp. A transducer 36 which measures displacement or force is located to measure the lateral position of this dimensionally stable tube portion or the force to maintain this position. Because the clamp of the present invention provides such an unusual degree of stability, measurement of movement or of change in force of the tube wall by the transducer provides a measurement of fluid pressure within the tubing. This is an important indication of vein collapse or clotting where the needle of the IV set is inserted into the patient. The invention allows this measurement without any in-line devices.

FIG. 4a–e show the clamp 30 of FIG. 3a applied across a segment of PVC tubing 12 that is normally in a cylindrical configuration. As the plates 32 are forced together, it is believed that compressive stress, indicated by the solid black triangles 43, forms at the outer walls 42 of the tubing and tensile stress indicated by outline triangles 45, form at the inner walls 44. These wall stresses cause viscoelastic tubing material to flow away from the zone of compressed tubing portions 12b, 12b. FIG. 4a demonstrates the relative compressive and tensile stresses when the plates 32 begin to compress the tubing. FIG. 4b shows the relative stresses when the tubing 12 is compressed to the point where the opposing walls just touch. As shown in FIG. 4c, increasing the compression decreases the tubing wall thickness under the plates 32 and forces the tubing material 12 to bend slightly outwardly into the central cavity formed by the recesses 34, 34 thereby forming the flow orifice 24.

Figure 4D:
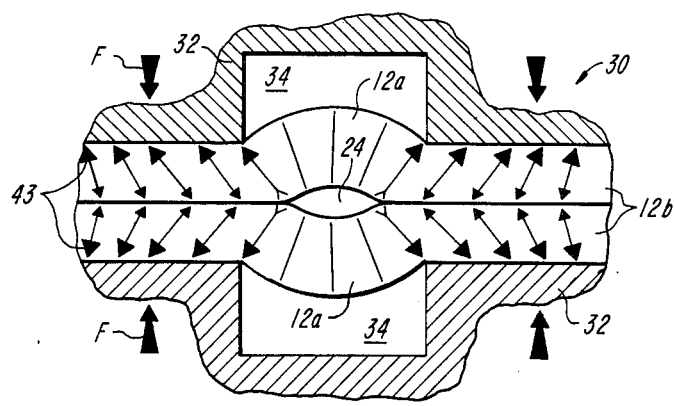
Figure 4E:
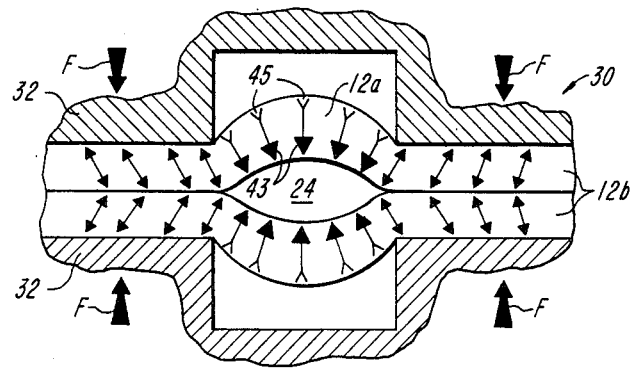

As shown in FIG. 4d, increasing the compressive force decreases the wall thickness of the tubing 12 and forces the tubing 12 to bend further outwardly into the central cavity until the compressive and tensile stresses within the tubing wall portions 12a, 12a are in equilibrium in accordance with the present invention. If the recesses 34, 34 are configured and dimensioned so that they do not confine or support the tubing portions 12a, 12a, and if still more compressive force is applied, as shown in FIG. 4e, the tubing 12 will continue to expand into the cut out sections 34 and larger tensile and compressive stresses will form within the tube disturbing the equilibrium and causing the tubing 12 to creep and continue to expand outwardly into the cut out sections 34. Overcompression results in an undesirable increase in the flow rate over time.

FIG. 4a to 4d demonstrate the method of the present invention for regulating fluid flow. Contrary to what one would expect, a stable orifice is created at the center of a deformable tubing by compressing the tubing with sufficient stress that the tubing is initially completely closed, and then opens. When opened, the internal stresses are in equilibrium. This is in sharp contrast to most prior art devices which begin with an open, undeformed tubing and then compress it to reduce the cross-sectional area of the internal flow path, but not close it off entirely and certainly not close it off entirely and then reopen it with increased compression.

Flow rate can be usd to monitor the various stages of compression. When the tubing is first deformed, the orifice is wide open and fluid streams through the tubing. If the amount of compression is increased, the flow rate drops initially, but then continues to decrease at a fairly rapid rate. If the tubing is compressed until the walls are almost completely touching, the flow rate is initially very low but then also continues to decrease. These two situations are also characteristic of conventional prior art clamps used to regulate IV flow. As the tubing is compressed still further, the orifice 24 begins to open and the flow rate increases. If the compression is too low, the flow rate is not stable and it steadily declines. If the compression is at the proper level, stress equilibrium is reached rapidly and the flow rate is stable. This point is dependent on factors such as the tubing size, the material, the width and height of the opening into which the tubing can expand, etc. If the tubing is compressed too much, the flow rate will again become unstable, but this time the flow rate typically increases over time since the orifice will continue to creep.

Figure 5:
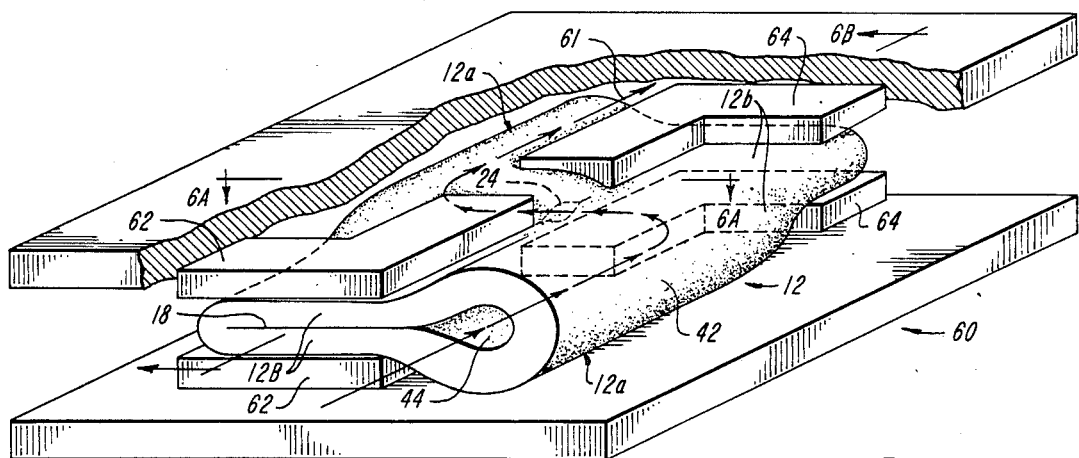
FIG. 5 is a perspective view of a clamp consisting of two L-shaped clamp members positioned at separate points along a length of tubing which apply normal compressive forces to opposite sides of the tubing to form an S-shaped flow path between the two clamp members.

FIG. 5 shows the preferred apparatus embodiment of this invention, a clamp 60 in which the tubing 12 is clamped from opposite sides at two axially displaced locations to create a generally "S-shaped" flow path 61 with a transverse orifice 24. More specifically, members 62 and 64 each have a pair of clamping plates that act on opposite exterior surfaces of one edge portion 12b, 12b of the tubing. The clamp members each compress the tubing to produce a degree of compression characteristic of this invention in a corresponding L-shaped (or 90°) configuration when viewed from the top of the clamp. FIG. 6a is a simplified top plan view that more clearly demonstrates the flow path through the clamp 60. Once an orifice is formed, the flow rate may be adjusted by changing the relative positions of the clamps 62 and 64, the level of the compressive force, or by using an adjusting mechanism such as a pivotable lever 66 shown in FIG. 7a. Changing the angular position of the pivot changes the size of the opening into which the tube can expand.

Figure 7C:
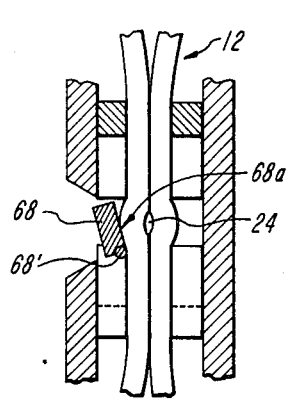
FIG. 7a is the device of FIG. 6b including a pivotable adjusting lever.
FIG. 7b is a view in perspective of the clamp shown in FIGS. 6a and 6b but with a rotating cam member to adjust the size of the flow orifice.

An exterior cam adjustment mechanism is illustrated in FIGS. 7b and 7c. A cam assembly 67 is rotatably supported at end mounts 67a and 67b in the clamp body. A cam support bar 67c extends across the tubing between the end mounts. A cam member 68 is carried on the support and positioned, in the preferred form shown, to act on the tubing at a point directly over the orifice 24. As is best seen in FIG. 7c, the axis of rotation is located at one edge 68' of a cam surface 68a so that rotation of the cam assembly 67 applies a varying force on the outer surface of the tubing. This adjusts the internal cross sectional area of the orifice as a function of the angular position of the cam.

Figure 8:
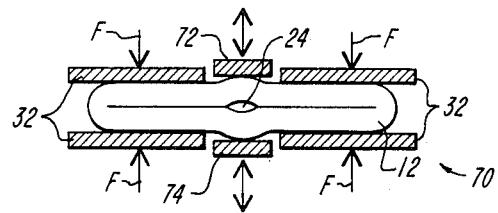
FIG. 8 is a cross-sectional view of a flow control clamp consisting of two sets of opposing flat plates with central recesses, the central flow orifice being adjusted by opposing flat barriers.

Other embodiments of a flow control clamp according to this invention are shown in FIGS. 8–13. FIG. 8 shows a variation of the clamp 30 of FIG. 3 where the recesses 34 in the plates 32 are replaced with adjustable barrier plates 72 and 74. These adjustable barriers 72 and 74 control the extent to which the tubing 12 is compressed and the extent to which the orifice 24 can expand.

Figure 9A:
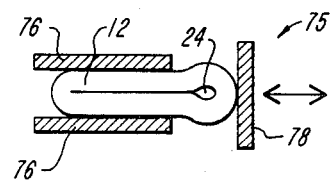
FIG. 9a is a cross-sectional view of a clamp consisting of two opposing flat plates to compress two opposite tubing walls along one side of the tubing and an adjustable end barrier oriented generally perpendicular to the plates to control the expansion of the orifice in the unclamped portion of the tubing.
Figure 9B:
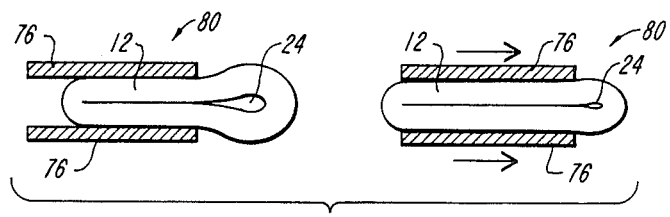
FIG. 9b is a cross-sectional view of a clamp consisting of two opposing flat plates that apply a vertical compressive force to two opposite tubing walls at one side of the tubing and which can be adjustably moved laterally across the tubing.
Figure 10A:
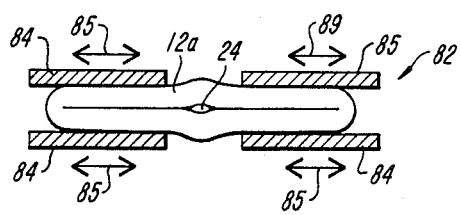
FIG. 10a is a cross-sectional view of a clamp which consists of two sets of opposing flat plates which apply both vertical and lateral compressive forces to the tubing to form a central orifice and to control the size of the orifice.
Figure 10B:
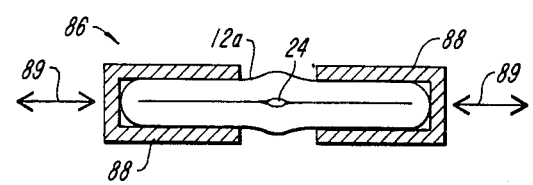
FIG. 10b is a cross-sectional view of a clamp consisting of two U-shaped clamp members which apply both vertical and lateral compression to the tubing to form a central orifice and to control the size of the orifice.

FIGS. 9a through 10b illustrate side-clamping flow-control devices according to the present invention where a compressive force is exerted only on the tubing walls along one side of the tubing. In FIG. 9a, a clamp 75 has two flat plates 76 which deform and compress one side of the tubing 12. A third plate 78 applies a lateral compressive force on the other, unclamped side of the tubing 12 that defines the orifice 24. The plate 78 assists in forming the orifice and provides a way to adjust the size of the orifice once formed. FIG. 9b shows a clamp 80 consisting solely of the two plates 76, wherein the plates 76 are slidably adjusted to move the point of application of compressive force on the tubing thereby adjusting the size of the orifice. The left hand view of the clamp 80 in FIG. 9b shows one adjustment position, and the right hand view shows a second adjustment position to reduce the size of the orifice 24. A clamp 82 shown in FIG. 10a utilizes two opposing pairs of compressive plates 84 to apply both vertical and lateral compressive forces, the lateral forces being generated by a lateral movement of one or both opposed pairs of the plates 84 along the direction of the arrows 85. This lateral movement can assist in forming the orifice 24 and in stabilizing it. FIG. 10b shows a clamp 86 where two U-shaped clamp members 88 apply both the vertical and lateral compressive forces on the tubing 12 thereby to form and adjust the orifice 24. The lateral compressive force, as with the FIG. 10a embodiment is developed by a lateral movement of one or both of the members 88 in the direction of arrows 89.

Figure 11A:
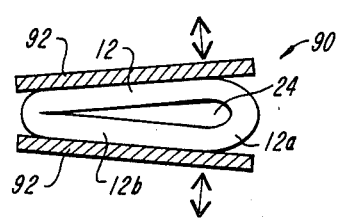
FIG. 11a is a cross-sectional view of a clamp according to this invention that utilizes two non-parallel flat plates.
Figure 11B:
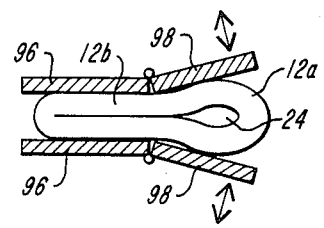
FIG. 11b is a cross-sectional view of a clamp where two flat plates compress opposite tubing walls at one side of the tubing and two other opposed non-parallel plates are angled to control the orifice size.

As shown in FIG. 11a and 11b, a simple flow control clamp 90, similar to that shown in FIG. 9b, has two flat plates 92 that are mutually inclined with respect to each other. Adjustment of the angle of inclination adjusts the amount of compression and the size of the orifice 24. FIG. 11b shows a clamp 94 which is a variation of the clamp 90 shown in FIG. 11a. It consists of a pair of parallel opposing plates 96 compressed at one side of the tubing 16 and two barriers 98 placed in an angular relationship to each other to limit the degree of expansion of the tubing 12 which forms the orifice 24. Adjustment of the angle of the barrier plates controls the size of the orifice.

FIG. 11c shows a modification of a side clamp where at least one of the clamp plates, as shown the upper plate 96′, has an inclined portion 97, adjacent the orifice 24 terminating in a recess 97a. As with other inclined clamp portions discussed above, this arrangement generates a sufficient stress to produce the operational features of the present invention while reducing the required total applied force F.

FIG. 11d shows a clamp similar to the clamp shown in FIG. 11b except that the inclined barrier plates 98′ extend between the tubing and the clamping members and are formed of a resilient material. Movement of the ends of the plates 98′ as indicated by arrows 99 allows an adjustment of the dimensions of the orifice 24 after it has stabilized.

As shown in FIG. 12a, a very low cost embodiment 100 of clamp 90 uses a plate 102 with a closed, internal slot 104 with angled side walls to compress the tubing 12 held in the slot 104 on one side 12b and not on the other side 12a. The exact angle and length of the slot 104 must be determined for the diameter, wall thickness, and material used to form the tubing to be clamped. The orifice 24 is adjusted by sliding the clamp to relocate the slot 104 relatie to the tubing.

In a preferred form of this low cost embodiment shown in FIG. 12b, the tubing walls 12b, 12b are clamped by sliding the tubing 12 so that most of the tubing lies between a pair of generally parallel side walls 104a, 104a that are separated a distance sufficient to close off any fluid flow between the walls. For conventional 0.125 inch inner diameter PVC tubing this distance is preferably 0.040 inch. Side walls 104b, 104b and 104c, 104c, as shown, are angled toward the tubing to produce a clamping between these wall portions that produces the additional compressive force characteristic of this invention. The mutually inclined orientation of these wall pairs 104b, 104b and 104c, 104c also provides the benefits of a lower overall clamping force discussed above with respect to other embodiments. Mutually inclined side walls, 104d, 104d extend from the walls 104c, 104c to provide an exterior fixed limiting element on the expansion of the orifice 24, and in cooperation with the action of the stresses introduced by the walls 104b, 104b and 104c, 104c adjust the size of the surface in response to a movement of the tubing within the clamp along the direction of the arrow 105. For the aforementioned PVC tubing, the walls 104b, 104b preferably each slope at a 10° angle to a minimum separation of 0.030 inch, the walls 104c, 104c. slope at 5°, and the walls 104d, 104d each slope at 10° to a maximum separation of 0.120 inch.

FIG. 13 illustrates another embodiment 110 of the present invention consisting of three clamp elements 112 which converge radially on the tubing to form the orifice 24. Preferably the elements 112 are of the same configuration and dimensions and they are equiangularly spaced to produce a symmetry and equality in the applied compressive forces at the compressed wall portions 12b, 12b.

Flow studies were conducted to compare the performance of flow regulating clamps according to the present invention with a prior art regulating clamps which is currently on the market and is of the type described in U.S. Pat. No. 4,047,694 to Adelberg. The studies were conducted using standard PVC tubing connected to an i.v. bottle with a starting one meter hydrostatic head pressure. The flow rate was calculated by converting the drops/hr. to ml./hr. using the manufacturer's conversion rate of 15 drops/ml. The test fluid was water.

Figure 15:
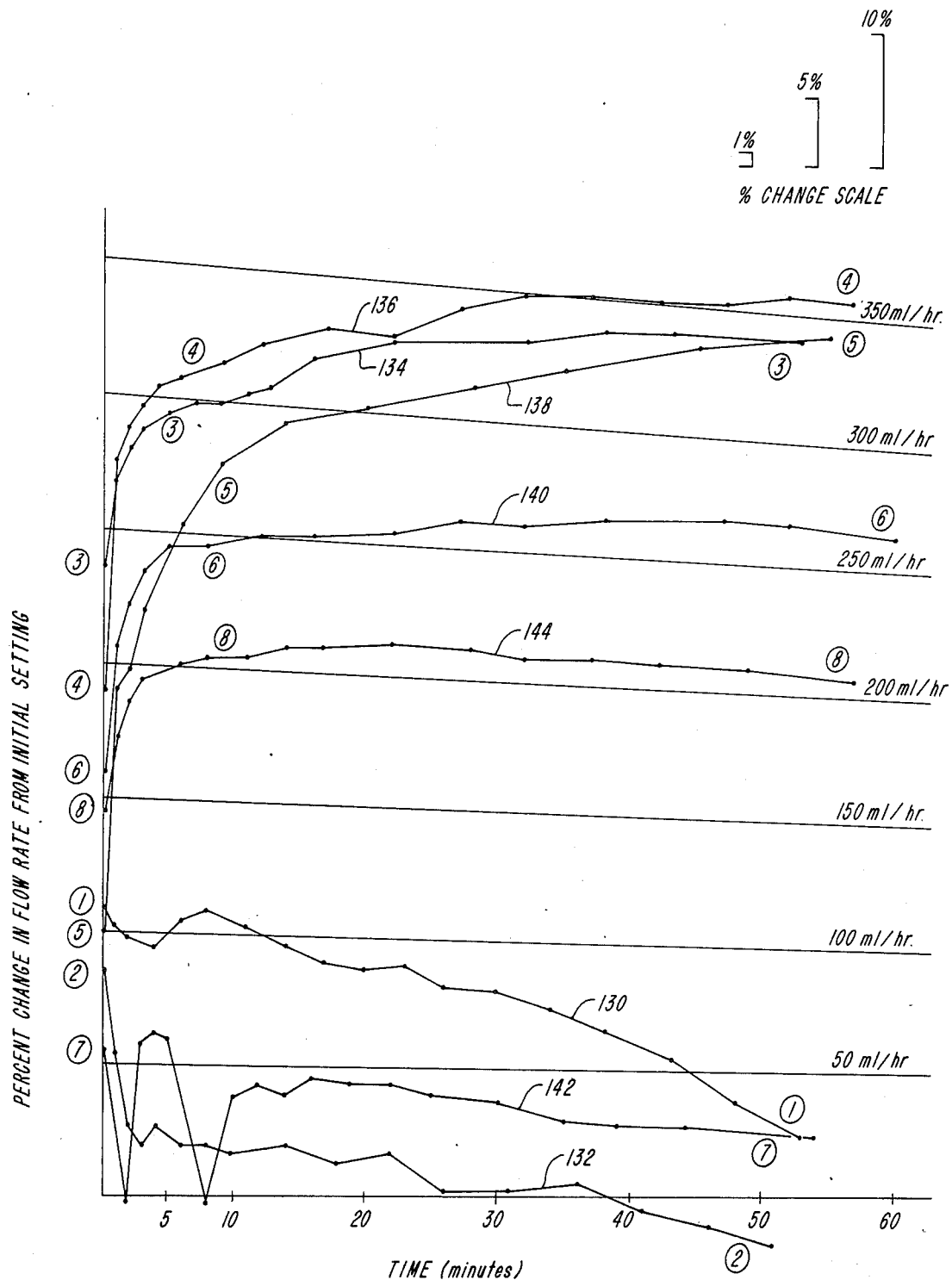
FIG. 15 is a graph of the percent change in flow rate versus time in minutes for a prior art roller clamp.

The results are shown in FIGS. 14 and 15. FIG. 14 is a graph of the percent change in flow rate after initial setting versus time (minutes) for the device of FIG. 3b (lines 120,122), the side clamp device of FIG. 9b (line 124) and the side clamp device of FIG. 11c (lines 126, 128) set at starting flow rates of approximately 50 mls/hr, 150 mls/hr, 150 mls/hr, 195 mls/hr, and 250 mls/hr, respectively. In each case, there was less than 6% change from the starting flow rate over a period of a least one hour. The series of straight lines are for reference, showing the rate of change in flow for an ideal orifice as the hydrostatic pressure decreases due to dispensed fluid.

The device used to generate lines 120 and 122, as shown in FIG. 3b is characterized by two angled clamps which compress compresses the tubing (O.D. 0.170 inch, wall thickness 0.024 inch) to a total thickness of 0.032 inch to 0.037 inch (120) and 0.030 inch to 0.035 inch (122). Both clamps have a 5 degree slope inwardly away from the orifice, but differ by the amount of compression. The device used to generate line 124 is a side clamp device which comprises the tubing to a total thickness of 0.037 inch. The device used to generate lines 126 and 128 is similar to this device except that the upper compression plate is angled 5 degrees inwardly away from the orifice, as was the device used to generate line 120. As is readily apparent, regardless of the initial flow rate, the flow rate remains remarkably constant over time.

FIG. 15 is a graph of the percent change in flow rate from initial setting versus time (minutes) for the prior art roller device. The same device was used to control flow rate for a series of runs (lines 130, 132, 134, 136, 138, 140, 142, 144), with starting flow rates of approximately 110 mls/hr, 90 mls/hr, 240 mls/hr, 190 mls/hr, 100 mls/hr, 160 mls/hr, 55 mls/hr, and 145 mls/hr, respectively. The flow rate changed from as little as 11% of the starting flow rate to as much as 44%. Regardless of the degree of change, these data establish that the clamp is not stable over time during a single run and it performs inconsistently and unpredictably from run to run. The results demonstrate the dramatically greater stability over time for the devices according to the present invention when compared to the prior art devices.

These embodiments and other modifications of the flow control device and the method for regulating fluid flow of the present invention will occur to those skilled in the art from the foregoing detailed description and accompanying drawings. Such modifications and variations are intended to fall within the scope of the appended claims.

What is claimed is:

1. A method for producing a time-stable orifice within a deformable tubing with a fluid flow through said orifice comprising thesteps of placing the inner surfaces of at least a first portion of the tubing into contact with one another in a plane of contact, and generating a compressive stress within the walls of the contacting tubing portions that causes a second portion of the tubing walls adjacent the first portion to curve away from said plane of contact to form said orifice, said compressive stress being of a value that the net stresses within the tubing wall that defines said orifice are generally in equilibrium after said curvature, wherin an increase in said compressive stress increases the flow rate of said fluid through said orifice and a decrease in said compressive stress decrease said flow rate.

2. The method of claim 1 further comprising the steps of limiting said curvature of said second tubing portion to form said orifice.

3. The method of claim 2 wherein said limiting is adjustable to set the cross-sectional area of said orifice to a desired value.

4. The method of claim 1 further comprising the step of applying said compressive stress to said tubing walls over a small area to reduce the force required to generate said compressive stress.

5. The method of claim 1 wherein said generating comprises applying a compressive force across said first portion of said tubing at at least a site adjacent said second portion, said compressive force reducing the thickness of said tubing walls at said site.

6. The method of claim 5 wherein said generating also includes applying a lateral compressive stress directed generally parallel to the plane of contact.

7. The method of claim 1 wherein said generating includes the generating of both laterally directed and axially directed compressive stresses and where the axial compressive stresses are the principal stresses causing said curvature to define said orifice.

8. The method of claim 7 wherein said generating further comprises generating said compressive and axial stresses at two locations along the length of the tubing and at opposite sides of said tubing to form two lumens for fluid flow therethrough at opposite sides of said tubing and said orifice providing a flow path connectig said side lumens where the flow through said orifice is non-parallel to the longitudinal axis of said tubing.

9. The method of claim 1 wherein said placing and said generating of a compressive stress is due to a clamping of tubing walls at one side of the tubing and wherein said orifice forms on the other side of the tubing.

10. The method of claim 1 wherein said placing and generating of said compressive stress is due to a clamping of tubing walls at opposite sides of said tubing and wherein said orifice forms in the middle of said tubing.

11. The method of claim 1 wherein said generating produces stresses within said second tubing portion causing said curvature, that are symmetrical prior to said equilibrium with respect to axes lying in the plane of contact that are parallel to and orthogonal to the longitudinal axis of said tubing.

12. Means for producing a dimensionally time-stable orifice within a deformable tubing with a fluid flow through said orifice comprising means for transmitting a compressive force to the tubing wall, said force transmitting means being configured and positioned with respect to said tubing to close the inner surfaces of at least a first portion of the tubing into contact with one another at a plane of contact, means for driving said force transmitting means to produce said closing and then produce an additional force that in combination with said force transmitting means produces a compressive stress in said first tubing portion, said force transmitting means also being configured and positioned with respect to said tubing to allow an outward curvature of at least a second portion of said tubing walls away from said plane of contact in response to said compressive stress to produce said orifice, said tubing being generally in a stress equilibrium following said outward curvature, said driving means and said force transmitting means creating an overcompression in said first tubing portion such that an increase in said compressive stress increases the flow rate of said fluid through said orifice and a decrease in said compressive stress decreases said flow rate.

13. The means of claim 12 wherein said force transmitting means comprises a clamp having at least two opposed clamping members that lie on opposite sides of said first tubing portion.

14. The means of claim 13 further comprising means exterior to said tubing for limiting said curvature.

15. The means of claim 14 wherein said limiting means are fixed.

16. The means of claim 15 wherein said limiting means comprises a pair of mutually inclined members disposed on opposite sides of said second tubing portion and defining a region that widens in a direction away from said first tubing portion.

17. The means of claim 16 wherein said limiting means comprises at least one rigid barrier plate positioned to act on the outer surface of said second tubing portion.

18. The means of claim 14 wherein said limiting means is adjustable to alter the dimensions of said orifice once formed.

19. The means of claim 18 wherein said adjustable limiting means comprises a rigid member that has a portion that engages said second tubing portion and is movable to displace the wall of said second tubing portion.

20. The means of claim 19 wherein said rigid member is a rotatable shaft that includes a cam surface secured thereon such that changes the angular portion of said rigid member produce corresponding changes in the cross-sectional flow area of said orifice.

21. The means of claim 16 wherein said inclination is in a direction that produces a lateral compressive stress directed generally along said plane of contact and transversely to the longitudinal axis of said tubing to push tubing material toward said second tubing portion.

22. The means of claim 13 wherein at a portion of at least one of said clamping plates has a surface adjacent said second tubing portion that is inclined to reduce the surface area over which the force generated by said driving means is applied to said first tubing portion.

23. The means of claim 13 further comprising means for limiting the maximum value of said copressive force.

24. The means of claim 14 wherein said limiting means comprises stop surfaces formed on said clamping members.

25. The means of claim 13 wherein said clamping plates each have facing central recesses so that there are two first tubing portions along opposite sides of the tubing and said orifice is formed within a cavity formed by said recesses.

26. The means of claim 13 wherein said clamping members act as a side clamp such that said first tubing portion includes two thicknesses of tubing wall along one side of said tubing and said second tubing portion lies on the opposite side of said tubing.

27. The means of claim 26 wherein said clamping plates are generally parallel to one another.

28. The means of claim 26 wherein said clamping plates are mutually inclined with respect to one another.

29. The means of claim 26 wherein there are two of said side clamps each acting on opposite sides of said tubing and being spaced from one another longitudinally along said tubing to generate components of said compressive stress along both said longitudinal axis and in a direction generally transverse to said longitudinal axis, whereby said side clamps form flow lumens along opposite sides of said tubing and said orifice provides a transversely oriented path connecting said lumens.

30. The means of claim 29 wherein at least one of said clamping plates in each of said side clamps has an L-shaped configuration in said contact plane and wherein at least a portion of one of said clamping plates of each of said side clamps adjacent said second tubing portion is inclined inwardly away from said orifice.

31. The means of claim 26 wherein said clamping members are side walls of a slot formed in a plate member, said slot having a region of reduced slot width where said tubing walls are closed and compressd and a region of increased slot width where said curvature can occur to form said orifice, said tubing being slidable within said slot between said regions to adjust the size of said orifice.

* * * * *